United States Patent [19]

Suresh et al.

[11] 4,290,920
[45] Sep. 22, 1981

[54] SB-CONTAINING CATALYSTS BY SB-OXIDE IMPREGNATION

[75] Inventors: Dev D. Suresh, Macedonia; James F. Brazdil, Lyndhurst; Robert K. Grasselli, Chagrin Falls, all of Ohio

[73] Assignee: The Standard Oil Co., Cleveland, Ohio

[21] Appl. No.: 107,942

[22] Filed: Dec. 28, 1979

[51] Int. Cl.$^3$ .................. B01J 27/02; B01J 23/10; B01J 23/84; B01J 23/64
[52] U.S. Cl. .................. 252/439; 252/462; 252/468; 252/469; 252/470
[58] Field of Search .............. 252/439, 462, 468, 469, 252/470

[56] References Cited

U.S. PATENT DOCUMENTS

| | | | |
|---|---|---|---|
| 3,325,504 | 6/1967 | Grasselli | 252/470X |
| 3,328,315 | 6/1967 | Callahan et al. | 252/470 |
| 3,338,952 | 8/1967 | Callahan et al. | 252/470 |
| 3,431,292 | 3/1969 | Callahan et al. | 260/465.3 |
| 3,637,797 | 1/1972 | Decker et al. | 252/469 X |

Primary Examiner—Delbert E. Gantz
Assistant Examiner—William G. Wright
Attorney, Agent, or Firm—John E. Miller, Jr.; Herbert D. Knudsen; Larry W. Evans

[57] ABSTRACT

Antimony-based oxide complex catalysts are improved by adding to these catalysts an antimony-containing compound such as $Sb_2O_3$.

17 Claims, No Drawings

SB-CONTAINING CATALYSTS BY SB-OXIDE IMPREGNATION

BACKGROUND OF THE INVENTION

The present invention relates to a technique for improving the catalytic properties of various antimony-containing oxide complex oxidation catalysts.

Oxidation catalysts in which antimony forms an integral part of the base catalyst system have been used for various types of oxidation reactions, e.g. oxidation of olefins to produce aldehydes and acids, ammoxidation of olefins to produce unsaturated nitriles and oxydehydrogenation of olefins to produce diolefins such as isoprene. For example, note U.S. Pat. No. 3,431,292, which discloses various uranium antimonate catalysts useful in various oxidation reactions, U.S. Pat. No. 3,338,952, which discloses iron antimonate catalysts useful in various oxidation reactions, and U.S. Pat. No. 3,296,957, which discloses various tin antimonate catalysts useful in various oxidation reactions. The disclosures of all these patents are incorporated herein by reference.

While catalysts described in the prior art are capable of providing good yields of the desired end products, it is always beneficial to improve the performance of catalysts so that they can provide even better yields.

Accordingly, it is an object of the present invention to provide a technique for forming new antimony-containing oxide complex oxidation catalysts which yield catalysts having improved catalytic properties.

In addition, it is a further object of the invention to provide a novel technique for processing used antimony-containing oxide complex catalysts to rejuvenate the catalytic properties thereof.

SUMMARY OF THE INVENTION

These and other objects are accomplished by the present invention which is based on the discovery that the catalytic properties of various antimony-containing oxide complex oxidation catalysts can be improved by adding to these catalysts an antimony compound.

Thus, the present invention provides a process for improving the catalytic performance of an antimony-containing oxide complex catalyst comprising adding to the catalyst an antimony-containing compound in an amount such that the amount of antimony added to the catalyst is 0.1% to 25% based on the antimony in the catalyst.

DETAILED DESCRIPTION

Catalysts

The present invention can be practiced on any antimony-containing oxide complex catalyst, whether new or used. The invention is preferably practiced on "antimony-based" catalysts, i.e. catalysts which contain at least about 20 atom percent antimony based on the total atoms in the catalyst, excluding oxygen and, of course, excluding any support which might be used. Such catalysts are well known and described inter alia in the patents mentioned above.

For convenience, these catalysts can be described as oxide complexes of the formula:

wherein

M is U, Fe, Mn, Ce, Th, Sn, Ti or mixtures thereof, preferably U, Fe, Sn or mixtures thereof;

A is Mo, W or mixtures thereof;

B is V, Te, Cr, Cu, Bi or mixtures thereof; and

C is Ni, Co, alkali metal, alkaline earth metal or mixtures thereof; and wherein $0 \leq a \leq 10$;
$0 \leq b \leq 10$;
$0 \leq c \leq 10$;
$0.1 \leq c \leq 10$;
$5 \leq e \leq 100$; and x is a number sufficient to satisfy the valence requirements of the other elements present.

Preferably
$0 \leq a \leq 5$;
$0 \leq b \leq 5$;
$0 \leq c \leq 5$; and
$0.1 \leq d \leq 10$.

As previously indicated, preferred catalysts processed by the present invention are those whose antimony content is at least 20 atom percent based on the total number of atoms in the oxide complex excluding oxygen. Most preferably, the amount of antimony in the oxide complex is at least 35%, even more preferably 50% based on the number of atoms in the complex excluding oxygen.

A preferred group of catalysts are those in which M is U, Fe, Sn or mixtures thereof, and further wherein c/d equals 1/3 to 1/6, preferably 1/4 to 1/5.

As indicated above, the oxide complex catalysts used in the present invention can be supported on a support, as is conventional. Any known support, such as silica, alumina, Alundum, graphite, titania, zirconia and the like, can be used. It will be understood that the various proportions, ratios and percentages given in this specification are made with respect to the oxide complex, the support being excluded.

Antimony-Containing Compound

In accordance with the present invention, antimony-containing oxide complex catalysts as described above are impregnated with (i.e. mixed with) an antimony-containing compound. Usually, the antimony compound will be an oxide of antimony such as $Sb_2O_3$, $Sb_2O_4$ and $Sb_2O_5$. Other antimony-containing compounds, however, can be used. For example, antimony halides such as $SbCl_2$, $SbCl_3$, $SbCl_5$ and $SbF_5$ can be used as well as various antimony-containg organo-metallic compounds such as $Ph_3Sb$, $Et_4SbCl$, $Me_4SbI$ (wherein Ph is phenyl, Et is ethyl and Me is methyl). In accordance with one embodiment of the invention, various metal antimonates can be used. In this situation, it is desirable that the metal in the metal antimonate also be a component of the antimony-based oxide complex being treated. For example, if the antimony-based catalyst being processed is a complex iron antimonate, it is appropriate to use iron antimonate as the antimony compound. Examples of various metal antimonates which can be employed are $VSbO_4$, $NiSb_2O_6$, $CoSb_2O_6$, $MnSbO_4$, $Fe_2Sb_2O_7$, $FeSb_2O_6$, $USb_3O_{10}$ and the like.

It is also possible to use antimony compounds containing metals other than those in the oxide complex. It is desirable, however, to avoid using compounds containing elements which will poison the catalyst.

Means Of Impregnation

The antimony-containing compound can be added to the antimony-containing oxide complex catalyst processed in accordance with the present invention in any manner. If the antimony-containing compound is a liquid, then it is easiest simply to use that compound as is. Normally, however, the antimony-containing compound will be a solid, and in this situation the compound can easily be employed by forming an aqueous slurry of a fine powder of the compound. In accordance with this procedure, it is desirable to form a powder of the compound having a particle size of below 40 microns, preferably below 20 microns. This powder can then be easily formed into an aqueous slurry having a solids content preferably below 50, more preferably below 20 weight percent. Such a slurry can then be easily applied to the antimony-containing oxide complex to impregnate the same with the antimony-containing compound.

Still another technique for adding the antimony compound is to dissolve or disperse the antimony compound in an organic medium and impregnate the catalyst with this solution and/or dispersion. Organic media such as organic acids and organic nitriles have been found useful for this purpose. Also useful are aqueous ammonia and anhydrous ammonia. Also, the antimony compound if in powder form can be simply charged into an operating reactor containing an antimony-containing catalyst.

In a preferred embodiment of the invention, the impregnant is applied by means of an aqueous nitric acid solution. The presence of nitric acid in the aqueous slurry is beneficial because it causes or promotes oxidation of $Sb^{+3}$ to higher valence states. Since antimony-based oxide complex catalysts seem to exhibit better catalytic properties when antimony is in a higher valence state, it is desirable in accordance with the present invention that the antimony added to the oxidation catalyst also be in higher valence states. If a nitric acid aqueous slurry is used, the aqueous slurry should preferably be about 100 to 1, more preferably 50 to 1 weight percent in nitric acid.

Amount of Antimony Compound Added

The amount of antimony-containing compound impregnant deposited on the oxide complex catalyst can vary widely. Normally, the amount of impregnation will be such that the amount of antimony on an atomic basis added to the oxidation catalyst is between about 0.1 and 25% based on the number of atoms in the oxide complex. While less than 0.1% antimony can be added, the improvement realized is minimal, while greater than 25% impregnation also yields little if any improvement over a 25% impregnation. Preferably, the amount of impregnation is 0.5 to 20%, more preferably 2 to 10%, most preferably about 3 to 5%.

Post-Impregnation Processing

After the antimony-based oxidation catalyst is impregnated in accordance with the present invention, it is processed in the same way that catalyst precursors derived from aqueous slurries, i.e. the solids recovered from an aqueous slurry during catalyst preparation, are processed to form antimony-based oxidation catalysts. Thus, the impregnated oxidation catalyst is normally dried and then heated in elevated temperature in the presence of an oxygen-containing gas, usually air, for an extended period of time. In other words, the catalyst is subjected to conventional calcination. In carrying out this calcination, the catalyst is normally heated in air to temperatures ranging from 200° C. to 1,200° C. for periods of from 0.5 to 50 hours. Normally, the catalyst is heated to temperatures of 550° C. to 950° C. for periods of 0.2 to 3 hours. Of course, if the catalyst to be processed contains nitrates, as for example if a nitric acid aqueous slurry is employed for impregnation, then the catalyst can be subjected to a staged calcination as is conventional. As well known, in such a calcination procedure, the catalyst is first heated at a relatively low temperature, e.g. about 250° C. to 450° C., to decompose the nitrates therein and drive off the decomposition products and thereafter heated at a higher temperature to set the final catalytic structure of the catalyst.

Catalyst Uses

The impregnated catalyst produced in accordance with the present invention can be used in the same way and for the same purposes as known antimony-based oxidation catalysts. For example, they can be ideally used in the ammoxidation of propylene or isobutylene to acrylonitrile and methacrylonitrile respectively, the oxidation of olefins such as propylene and isobutylene to produce the corresponding unsaturated aldehydes and acids, and the oxydehydrogenation of various compounds such as isoamylene to produce the corresponding di-unsaturated compounds. The types of reactions these catalysts can be employed in and the way in which they can be used are exemplified in commonly assigned application Ser. No. 095,886, the disclosure of which is incorporated herein by reference.

WORKING EXAMPLES

In order to more thoroughly describe the present invention, the following working examples are presented. In these examples, various antimony-based oxidation catalysts were prepared. In addition, each of these catalysts was impregnated with $Sb_2O_3$ in accordance with the following procedure.

0.8 gms. of $Sb_2O_3$ was added to 50 ml. concentrated nitric acid and heated with stirring at 80° C. for approximately 2.0 hours. The slurry was then filtered and washed several times with distilled water. The filtrate so obtained was added to an aqueous slurry of 20 gms. of the indicated catalyst in 200 ml. of distilled water. The mixture was stirred and heated at 90° C. for 3 hours and then allowed to evaporate slowly to dryness. The residue was then heat treated at 290° C. for 3 hours to cause denitrification and then at 450° C. for 3 hours to form final calcination. The catalyst was then ground and screened and the portion of the catalyst having a particle size of from 20 to 35 mesh was recovered as the objective catalyst.

Each of the catalysts so produced as well as the corresponding unimpregnated antimony-based oxide catalyst were tested in the ammoxidation of propylene to produce acrylonitrile. In each test, 5 cc. of catalyst was charged into a 6.5 cc. micro-reactor and contacted with a feed containing 1 propylene/1.2 $NH_3$/10.5 air/4 $H_2O$ at 445° C.±15° C. at a 3 second contact time. The gross reaction product was recovered and analyzed for acrylonitrile yields. The results obtained are set forth in the following Table I.

TABLE I

| Example | Catalyst Composition | Unreacted Propylene | Acrylonitrile Yields* | Acrylonitrile Select.** |
|---|---|---|---|---|
| Comp. A | $Cr_{12}Sb_{14}Fe_1Mo_1O_x + SiO_2$ | 28.7 | 18.4 | 25.9 |
| 1 | Comp. A + $Sb_2O_3$ Impreg. | 39.4 | 30.3 | 49.9 |
| Comp. B | $Fe_{12}Sb_{25}Cu_3Te_2W_{0.2}Mo_1O_x + SiO_2$ | 4.7 | 76.4 | 80.1 |
| 2 | Comp. B + $Sb_2O_3$ Impreg. | 1.3 | 80.5 | 81.5 |
| Comp. C | $Fe_{12}Sb_{25}Cu_3Bi_2W_{0.2}Mo_1O_x + SiO_2$ | 1.3 | 75.4 | 76.4 |
| 3 | Comp. C + $Sb_2O_3$ Impreg. | 0.7 | 78.9 | 79.5 |

*Moles acrylonitrile produced divided by Moles propylene fed
**Moles acrylonitrile produced divided by Moles propylene reacted From the foregoing, it can be seen that catalysts impregnated with an antimony-containing compound provide acrylonitrile yields superior to those obtained from the antimony-based oxide complex catalyst itself. Thus, the present invention provides a simple and straightforward method for improving the catalytic properties of various antimony-containing catalysts.

Although only a few embodiments of the present invention have been described above, many modifications can be made without departing from the spirit and scope of the invention. All such modifications are intended to be included within the scope of the present invention, which is to be limited only by the following claims.

We claim:

1. A process for improving the catalytic performance of a used antimony-containing oxide complex catalyst comprising adding to said catalyst an antimony-containing compound in an amount such that the amount of antimony added to said catalyst is 0.1 to 25% based on the antimony in said catalyst.

2. The process of claim 1 wherein 25% to 10% antimony is added to said catalyst.

3. The process of claim 2 wherein said antimony-containing compound is an oxide of antimony.

4. The process of claim 3 wherein said antimony-containing compound is applied by means of an aqueous nitric acid slurry.

5. The process of claim 4 wherein said oxide complex catalyst is defined by the formula:

$$A_aB_bC_cM_dSb_eO_x$$

wherein
   M is U, Fe, Mn, Ce, Th, Sn, Ti or mixtures thereof;
   A is Mo, W or mixtures thereof;
   B is V, Te, Cr, Cu, Bi or mixtures thereof; and
   O is Ni, Co, alkali metal, alkaline earth Metal or mixtures thereof; and
wherein
   $0 \leq a \leq 10$;
   $0 \leq b \leq 10$;
   $0 \leq c \leq 10$;
   $0.1 \leq d \leq 10$;
   $5 \leq e \leq 100$; and
   x is a number sufficient to satisfy the valence requirements of the other elements present.

6. The process of claim 5 wherein M is Fe, Sn or mixtures thereof, and further wherein c/d is ⅓ to 1/6.

7. The process of claim 5 wherein $0 \leq a \leq 5$, $0 \leq b \leq 5$ and $0 \leq c \leq 5$.

8. The process of claim 1 wherein said catalyst is defined by the formula:

$$A_aB_bC_cM_dSb_eO_x$$

wherein
   M is U, Fe, Mn, Ce, Th, Sn, Ti or mixtures thereof;
   A is Mo, W or mixtures thereof;
   B is V, Te, Cr, Cu, Bi or mixtures thereof; and
   C is Ni, Co, alkali metal, alkaline earth metal or mixtures thereof; and
wherein
   $0 \leq a \leq 10$;
   $0 \leq b \leq 10$;
   $0 \leq c \leq 10$;
   $0.1 \leq d \leq 10$;
   $5 \leq e \leq 100$; and
   x is a number sufficient to satisfy the valence requirements of the other elements present.

9. The process of claim 1 further comprising heating said antimony-containing oxide complex catalyst after impregnation with said antimony-containing compound in air at 200° to 1200° C. for 0.5 to 50 hours.

10. An improved antimony-based oxidation catalyst comprising a used antimony-based oxide complex defined by the formula:

$$A_aB_bC_cM_dSb_eO_x$$

wherein
   M is U, Fe, Mn, Ce, Th, Sn, Ti or mixtures thereof;
   A is Mo, W or mixtures thereof;
   B is V, Te, Cr, Cu, Bi or mixtures thereof; and
   C is Ni, Co, alkali metal, alkaline earth metal or mixtures thereof; and
wherein
   $0 \leq a \leq 10$;
   $0 \leq b \leq 10$;
   $0 \leq c \leq 10$;
   $0.1 \leq d \leq 10$;
   $5 \leq e \leq 100$; and
   x is a number sufficient to satisfy the valence requirements of the other elements present.
impregnated with 0.1 to 25% of an antimony-containing compound impregnant, the percents being based on the atoms of antimony in the impregnant and the atoms of antimony in said oxide complex, said improved antimony-based oxidation catalyst capable of producing acrylonitrile in the ammoxidation of propylene in greater yields than said used oxide complex.

11. The improved catalysts of claim 9 wherein said impregnate is an oxide of antimony.

12. A process for improving the catalytic performance of an antimony-containing oxide complex catalyst defined by the formula:

$$A_aB_bC_cM_dSb_eO_x$$

wherein
   M is Fe, Mn, Ce, Th, Sn, Ti or mixtures thereof;
   A is Mo, W or mixtures thereof;

B is V, Te, Cr, Cu, Bi or mixtures thereof; and

C is Ni, Co, alkali metal, alkaline earth metal or mixtures thereof; and wherein $0 \leq a \leq 10$;

$0 \leq b \leq 10$;

$0 \leq c \leq 10$;

$0.1 \leq d \leq 10$;

$5 \leq e \leq 100$; and x is a number sufficient to satisfy the valence requirements of the other elements present, said process comprising adding to said catalyst an antimony-containing compound in an amount such that the amount of antimony added to said catalyst is 0.1 to 25% based on the antimony in said catalyst.

13. The process of claim 12 wherein M is Sn, Fe or mixtures thereof.

14. The process of claim 13 wherein said antimony-containing oxide complex catalyst is a used catalyst.

15. The product of the process of claim 14.

16. The product of the process of claim 13.

17. The product of the process of claim 12.